United States Patent [19]

Wuelknitz et al.

[11] Patent Number: 4,923,685

[45] Date of Patent: May 8, 1990

[54] ANTIMICROBIAL FLAVORED COMPOSITIONS HAVING PARTICULAR UTILITY AS MOUTH WASHES

[75] Inventors: Peter Wuelknitz, Duesseldorf-Benrath; Rudolf Lehmann, Leichlingen; Walter Ploeger, Hilden; Karlheinz Hill, Erkrath; Franz Förg, Langenfeld, all of Fed. Rep. of Germany

[73] Assignee: Henkel Kommanditgesellschaft auf Aktien, Duesseldorf, Fed. Rep. of Germany

[21] Appl. No.: 225,405

[22] Filed: Jul. 28, 1988

[30] Foreign Application Priority Data

Jul. 30, 1987 [DE] Fed. Rep. of Germany ....... 3725248

[51] Int. Cl.$^5$ ................................................. A61K 7/22
[52] U.S. Cl. ..................................... 424/54; 514/635; 514/901
[58] Field of Search .................... 424/49, 54; 514/635, 514/901

[56] References Cited

U.S. PATENT DOCUMENTS

| | | | |
|---|---|---|---|
| 2,684,924 | 7/1954 | Rose et al. | 167/30 |
| 2,990,425 | 6/1961 | Senior | 260/501 |
| 3,468,898 | 9/1969 | Cutler et al. | 260/301 |
| 3,547,828 | 12/1970 | Mansfield et al. | 252/351 |
| 3,707,535 | 12/1972 | Lew | 260/210 |
| 3,772,269 | 11/1973 | Lew | 260/210 |
| 3,804,946 | 4/1974 | Harrison et al. | 424/54 |
| 3,839,318 | 10/1974 | Mansfield | 260/210 |
| 3,842,168 | 10/1974 | Colodney | 424/54 |
| 3,843,779 | 10/1974 | Norfleet | 424/54 |
| 3,864,472 | 2/1975 | Pensak et al. | 424/54 |
| 3,934,002 | 1/1976 | Haefele | 424/54 |
| 3,937,805 | 2/1976 | Harrison | 424/54 |
| 3,937,807 | 2/1976 | Haefele | 424/54 |
| 3,947,570 | 3/1976 | Pensak et al. | 424/54 |
| 3,989,813 | 11/1976 | Januszewski et al. | 424/54 |
| 4,025,616 | 5/1977 | Haefele | 424/54 |
| 4,051,234 | 9/1977 | Gieske et al. | 424/54 |
| 4,053,636 | 10/1977 | Eustis, III et al. | 424/326 |
| 4,150,151 | 4/1979 | Pader et al. | 424/49 |
| 4,198,392 | 4/1980 | Juneja | 424/48 |
| 4,206,198 | 6/1980 | Schmolka | 424/49 |
| 4,241,049 | 12/1980 | Colodney et al. | 424/54 |
| 4,323,552 | 4/1982 | Schmolka | 424/54 |
| 4,343,785 | 8/1982 | Schmolka | 424/54 |
| 4,349,669 | 9/1982 | Klahr et al. | 536/127 |
| 4,476,107 | 10/1984 | Schmolka | 424/54 |
| 4,726,943 | 2/1988 | Klueppel et al. | 424/54 |
| 4,748,158 | 5/1988 | Biermann et al. | 514/635 |
| 4,820,507 | 4/1989 | Klueppel et al. | 424/54 |

FOREIGN PATENT DOCUMENTS

| | | | |
|---|---|---|---|
| 1145261 | 4/1983 | Canada | 424/54 |
| 0077167 | 4/1983 | European Pat. Off. | |
| 0705838 | 3/1954 | United Kingdom | |

*Primary Examiner*—Shep K. Rose
*Attorney, Agent, or Firm*—Ernest G. Szoke; Wayne C. Jaeschke; Norvell E. Wisdom, Jr.

[57] ABSTRACT

Aqueous homogeneous preparations containing 0.0025 to 0.1% by weight antimicrobial biguanide compounds, 0.005 to 0.2% by weight of an alkyl glycoside, 0.01 to 0.3% by weight of a water-insoluble aromatic oil, 0.01 to 0.3% by weight of a solubilizer from the group consisting of ethoxylated fatty acid glycerides, ethoxylated fatty acid sorbitan partial esters or fatty acid partial esters of glycerol or sorbitan ethoxylates show high activity despite the low concentration of antimicrobial biguanide compounds. The clear solubility is obtained without ethanol or with only very small contents of up to 15% by weight of ethanol. The preparations are particularly suitable as mouthwashes.

10 Claims, No Drawings

4,923,685

ANTIMICROBIAL FLAVORED COMPOSITIONS HAVING PARTICULAR UTILITY AS MOUTH WASHES

BACKGROUND OF THE INVENTION

1. Field of the Invention

This invention relates to aqueous preparations containing antimicrobial biguanide compounds, alkyl glycoside surfactants enhancing their effect and homogeneously solubilized water-insoluble aromatic oils which are particularly suitable for use as antiseptic mouthwashes.

Aqueous-alcoholic preparations of aromatic oils preferably containing antimicrobial compounds and surfactants are normally used as mouthwashes. The products are marketed either as clear or opaque, ready-to-use solutions which are used in undiluted form or preferably in the form of concentrates which have to be diluted to the in-use concentration with water before use.

It is an important objective to provide an adequate level of protection against the gram-positive bacteria with minimal concentrations of antibacterial compounds. Because gram-positive bacteria play a role in the formation of tartar and hence in the development of caries, their control is very important.

2. Statement of Related Art

It is known from EP-A-185 971 that this objective can be achieved by a combination of antibacterial biguanide compounds with alkyl glycoside surfactants. It is also known from U.S. Pat. No. 4,198,392 that certain biguanides can be used as oral compositions.

However, mouthwashes should contain organoleptically acceptable aromatic oils which, on the one hand, contribute towards the antimicrobial effect and, on the other hand, provide an agreeable and refreshing taste and impart a deodorizing effect while in use. Water-insoluble aromatic oils suitable for this purpose must be homogeneously solubilized in the mouthwash concentrate so that the concentrate and the in-use solution prepared therefrom remain stable and do not undergo premature separation. Lower pharmaceutically acceptable alcohols, particularly ethanol, and surfactants are normally used for this purpose. However, it is desirable to minimize the ethanol content both for reasons of cost and because of the irritation which relatively high concentrations of ethanol cause to the mucous membrane. This necessitates an increased content of particularly effective aromatic oil solubilizers. However, it has been found that many known solubilizers for aromatic oil reduce the potentiated antimicrobial effect of the system of antimicrobial biguanide compounds and alkyl glycoside surfactants. It is generally necessary as a result of this to increase the concentration of antimicrobial compounds or stronger bacteriacidal substances, for example hydrogen peroxide, or use of relatively high concentrations of ethanol to obtain an adequate antibacterial effect. However, such measures are extremely undesirable for compositions which are applied to the mucous membrane, particularly if they are applied over a relatively long period.

Accordingly, the object of the present invention is to provide flavored compositions containing a low concentration of antimicrobial biguanide compounds and homogeneously solubilized aromatic oils and, in the in-use concentration, no more than 15% by weight ethanol. It has been found that this object can be achieved particularly effectively using special solubilizers and by a specific choice of components both in type and in quantity.

DESCRIPTION OF THE INVENTION

Other than in the operating examples, or where otherwise indicated, all numbers expressing quantities of ingredients or reaction conditions used herein are to be understood as modified in all instances by the term "about".

The present invention relates to an aqueous, homogeneous composition containing an antimicrobial biguanide compound and an alkyl glycoside. These compositions comprise (A) from 0.0025 to 0.1% by weight of an antimicrobial biguanide compound, (B) from 0.005 to 0.2% by weight of an alkyl glycoside containing 8 to 16 C atoms in the alkyl group and having an average degree of oligomerization of the glycoside part of from 1 to 8, (C) from 0.01 to 0.3% by weight of a water-insoluble aromatic oil, (D) from 0.01 to 0.3% by weight of a solubilizer from the group consisting of ethoxylated fatty acid glycerides, ethoxylated fatty acid sorbitan partial esters or fatty acid partial esters of glycerol or sorbitan ethoxylates.

The composition according to the invention can contain substantially from 0.01 to 15% ethanol but are free of any other lower alkanols. The compositions are also free of other antimicrobial additives such as hydrogen peroxide or other peroxy compounds.

The antimicrobial biguanide compounds are preferably present in very low concentrations of from 0.0025 to 0.04% by weight. The antimicrobial biguanide compound preferably used is the 1,1'-hexamethylene-bis-(4-chlorophenyl)-biguanide ("chlorhexidine") disclosed in British Pat. No. 705,838 in the form of a water-soluble, physiologically compatible salt. These salts are, for example, preferably in the form of the acetate or the gluconate. Other antimicrobial biguanide compounds suitable for use in accordance with this invention are, for example, the polyhexamethylene biguanide compounds of the Vantocil ® I-B type (Imperial Chemical Industries), the 1,6-bis-(4-chlorobenzylbiguanido)-hexane (fluorhexidine) disclosed in German Pat. No. 1,964,196, and the antimicrobial biguanide compounds disclosed in U.S. Pat. No. 2,684,924, U.S. Pat. No. 2,990,425, U.S. Pat. No. 3,468,898, U.S. Pat. No. 4,022,834, U.S. Pat. No. 4,053,636 and U.S. Pat. No. 4,198,392. The disclosures of each of the above cited German and U.S. patents are incorporated by reference.

Alkyl glycosides, their production and their use as surfactants are disclosed in U.S. Pat. No. 3,839,318, U.S. Pat. No. 3,707,535, U.S. Pat. No. 3,547,828, U.S. Pat. No. 3,547,828, U.S. Pat. No. 3,772,269, U.S. Pat. No. 4,349,669 and in European patent application No. 77 167. All of these patents and patent applications are incorporated by reference. They are prepared by the reaction of glucose or oligosaccharides with primary $C_8$–$C_{16}$ alcohols. In respect to the glycoside component, both monoglycosides in which a cyclic sugar residue is attached to the fatty alcohol by a glycoside bond and also oligomeric glycosides having a degree of oligomerization of preferably up to 8 are suitable. Preferred alkyl glycosides for the production of the composition of this invention are those containing alkyl substituents having from 8 to 14 carbon atoms, having at least one branch in the alkyl group and an average degree of oligomerization of the glycoside component of from 1 to 4. The degree of oligomerization is a statistical mean value on which the homolog distribution typical of such technical products is based.

A particularly preferred alkyl glycoside is isotridecyl glucoside having a degree of oligomerization (OG) of approximately 3.

Suitable water-insoluble aromatic oils are any of the natural and synthetic flavorings commonly used for oral hygiene and dental care preparations. Natural flavorings may be used both in the form of essential oils isolated from the plants or plant parts in the form of the individual components isolated from those essential oils. The preparations according to the invention should preferably contain at lease one aromatic oil from the group consisting of peppermint oil, spearmint oil, anise oil, star anise oil, caraway oil, eucalyptus oil, fennel oil, cinnamon oil, clove oil, geranium oil, sage oil, pimento oil, thyme oil, marjoram oil, basil oil, citrus oil, wintergreen oil or one or more components of these oils isolated or synthetically prepared therefrom. The most important components of the oils mentioned are, for example, menthol, carvone, anethol, cineol, eugenol, cinnamaldehyde, caryophyllene, geraniol, citronellol, linalool, salven, thymol, terpinene, terpinol, methyl chavicol and methyl salicylate. Other suitable flavorings are, for example, menthyl acetate, vanillin, ionone, linalyl acetate, rhodinol and piperitone.

Solubilizers from the group of ethoxylated fatty acid glycerides comprise, above all, adducts of 20 to 60 mol ethylene oxide with mono- and diglycerides of linear $C_{12}$–$C_{18}$ fatty acids or with triglycerides of hydroxy fatty acids, such as hydroxystearic acid or ricinoleic acid. Other suitable solubilizers are ethoxylated fatty acid sorbitan partial esters, i.e. preferably adducts of 20 to 60 mol ethylene oxide with sorbitan monoesters and sorbitan diesters of $C_{12}$–$C_{18}$ fatty acids. Other suitable slubilizers are fatty acid partial esters of glycerol or sorbitan ethoxylates, i.e. preferably mono- and diesters of $C_{12}$–$C_{18}$ fatty acids and adducts of 20 to 60 mol ethylene oxide with 1 mol glycerol or with 1 mol sorbitol.

The preparation according to the invention preferably contain adducts of 20 to 60 mol ethylene oxide with hardened or unhardened caster oil (i.e. with hydroxystearic acid or ricinoleic acid triglyceride), with glycerol mono and/or distearate or with sorbitan mono- and/or distearate.

In addition to the necessary components mentioned, the preparations according to the invention may contain other known components of the type commonly used in antimirobial personal hygiene preparations for improving appearance, taste or handling. For example, physiologically safe dyes, opacifiers or pearlescers may be used for improving appearance. Natural or synthetic sweeteners preferably free from cariogenic carbohydrates may be added for improving taste. Such sweeteners include, for example, saccharin sodium, cyclamates, acesulfam potassium, Aspartame ® (L-aspartyl-L-phenylalanine methyl ester), glycerol, sorbitol, mannitol or xylitol.

The present invention also relates to concentrates of solid or liquid consistency which contain the necessary components A, B, C and D in such a concentration and in such a concentration ratio to one another that preparations according to the invention are obtained by dissolution of the concentrate in water or by dilution with water in a ratio by weight of 1:1 to 1:500.

If the concentrates are liquid for example, they may also contain more than 15% by weight ethanol if the ethanol concentration falls below 15% by or lower during the dilution with water to establish the in-use concentration.

If the concentrates are to be present, for example, in the form of powders, granulates or tablets, they contain in addition to the necessary components A, B, C and D solid or powder-form fillers and auxiliaries which either give the mixture a free-flowing powder-form structure or facilitate the preparation of free-flowing granulates or break-resistant tablets.

The powder-form fillers and auxiliaries may be, for example, powder-form sorbitol, mannitol or xylitol, water-soluble starch, powder-form silica gels (for example Aerosil), salts such as, for example, sodium chloride, sodium bicarbonate or magnesium sulfate. For the production of effervescent tablets which dissolve particularly quickly in water with evolution of carbon dioxide, combinations of sodium bicarbonate and powder-form organic acids, for example citric acid, tartaric acid or malic acid, may be present. The powder-form fillers and auxiliaries mentioned are preferably present in a quantity of from 80 to 98% by weight of the solid concentrate as a whole.

The preparations according to the invention and the liquid concentrates are prepared simply by dissolving the components in water. Solid granulates, tablets or effervescent tablets may be produced by the mixing, granulation or tabletting technique normally used for such products.

The following Examples are intended to illustrate the subject of the invention without limiting it in any way.

EXAMPLES

| 1. Mouthwash (in-use concentration) | | | | |
|---|---|---|---|---|
| | 1.1 | 1.2 | 1.3 | 1.4 |
| Ethanol (99%, non-denatured) | 5.0 | 5.0 | 10.0 | 10.0 |
| Chlorhexidine digluconate | 0.03 | 0.015 | 0.015 | 0.015 |
| Isotridecyl glucoside (OG = 3) | 0.01 | 0.01 | — | 0.1 |
| N-$C_{12}$-$C_{14}$-alkyl glucoside (OG = 2.2) | — | — | 0.2 | 0.5 |
| n-$C_8$-$C_{10}$-alkyl glucoside (OG = 1.8) | — | — | 0.1 | — |
| HR 60[1] | 0.1 | 0.1 | — | — |
| GMS 20[2] | — | — | 0.2 | 0.3 |
| Aromatic oil[3] | 0.1 | 0.1 | 0.2 | 0.3 |
| Dye blue[4] (1% in $H_2O$) | 0.1 | 0.1 | 0.1 | 0.1 |
| Sorbitol (70%) | 3.0 | 3.0 | 3.0 | 3.0 |
| Saccharin sodium | 0.05 | 0.05 | 0.05 | 0.05 |
| Water | ad 100 g | ad 100 g | ad 100 g | ad 100 g |

2. Mouthwash concentrates
2.1 Liquid concentrates

| | 2.1 20 x concentrate | 2.2 50 x concentrate |
|---|---|---|
| Ethanol (99%, non-denatured) | 40.0 g | 40.0 g |
| Isotridecyl glucoside (OG = 3) | 2.0 g | 2.0 g |
| HR 60[1] | 2.0 g | 5.0 g |
| Aromatic oil[3] | 2.0 g | 5.0 g |
| Dye blue[4] (1% in $H_2O$) | 1.0 g | 2.5 g |
| Chlorhexidine digluconate, 20% in $H_2O$ | 1.5 g | 3.75 g |
| Saccharin sodium | 1.0 g | 2.5 g |
| Water | 50.5 g | 36.25 g |
| | 100.0 g | 100.0 |

2.3 Powder-form, tablettable mouthwash concentrate (for dissolution in water in a ratio by weight of 1:100)

| | |
|---|---|
| Sorbitol (powder-form) | 50.0 g |
| $NaHCO_3$ | 19.0 g |
| Starch (water-soluble) | 1.0 g |

-continued

| Chlorhexidine acetate | 3.0 g |
| Isotridecyl glucoside (OG = 3) | 5.0 g |
| HR 60[1] | 1.0 g |
| Aromatic oil[3] | 1.0 g |
| Citric aicd | 20.0 g |

[1]adduct of 60 mol ethylene oxide with 1 mol hydrogenated castor oil
[2]adduct of 20 mol ethylene oxide with glycerol monostearate
[3]peppermint oil
[4]L-Blau 4 (Acid Blue 9, disodium salt, FD & C Blue No. 1, C.I. No. 42090)

3. Microbicidal activity

The microbicidal activity of the combinations according to the invention and of corresponding compositions, from which individual or compulsory components were missing, was tested against the following test germ suspensions:
(A) Staphylococcus aureus: $2 \times 10^9$ germs/ml
(B) Streptococcus mutans: $1 \times 10^9$ germs/ml The destruction times of the products to be tested were determined by the suspension test. Using water having a hardness of 17° Gh (German hardness), test solutions according to Table 1 were prepared, solutions 3.1 and 3.8 having the composition according to the invention.

At room temperature, quantities of 0.1 ml of the test germ suspension were pipetted into test tubes and mixed with quantities of 10 ml of the test solutions described above. After different contact times of up to 15 minutes, approx. 0.05 ml material was taken from the test tube twice using an inoculation loop and substrate cultures prepared both in liquid and on solid nutrient medium (agar). The cultures contained 3% Tween 80, 0.3% lecithin and 0.1% histidine as inactivators. The nutrient medium consisted of 3.0% by weight Casein-Soja-Bouillon (Merck) which, in the case of the solid nutrient medium, contained 1.2% by weight agar. The samples were incubated at 37°. After 2 days at the earliest, the cultures were macroscopically evaluated for growth and the destruction time or the residual germ content determined in this way.

In Table 1 below "−" means none, "+" less than 50, "++" less than 200 and "+++" more than 200 residual germs after the contact time and shown in brackets.

The results in Table 1 show that only compositions 3.1 and 3.8 according to the invention satisfy all requirements in regard to clarity, taste and adequate antibacterial activity.

We claim:

1. An aqueous homogeneous composition containing an antimicrobial biguanide compound and an alkyl glycoside, comprising
   (A) from about 0.0025 to about 0.1% by weight of an antimicrobial biguanide compound,
   (B) from about 0.005 to about 0.2% by weight of an alkyl glycoside containing 8 to 16 carbon atoms in the alkyl group and having an average degree of oligomerization of the glycoside commonent of from 1 to 8.
   (C) from about 0.01 to about 0.3% by weight of a water-insoluble aromatic oil,
   (D) from about 0.01 to about 0.3% by weight of a solubilizer selected from the group consisting of ethoxylated fatty acid sorbitan partial esters, fatty acid partial esters of glycerol, or sorbitan ethoxylates.

2. The composition of claim 1 additionally containing ethanol in an amount of about 15% by weight or less.

3. The composition of claim 1, wherein the antimicrobial biguanide compound is present in a quantity of from about 0.0025 to about 0.04% by weight.

4. The composition of claim 1 containing 1,1'-hexamethylene-bis-(4-chlorophenyl)-biguanide in the form of a water-insoluble, physiologically compatible salt as the antimicrobial biguanide compound.

5. The composition of claim 1, wherein the alkyl glycoside is one containing 8 to 14 carbon atoms in the alkyl and having at least one branch in the alkyl group and an average degree of oligomerization of the glycoside component of from 1 to 4.

6. The composition of claim 1, wherein the water-insoluble aromatic oil is selected from the group consisting of peppermint oil, spearmint oil, anise oil, star anise oil, caraway oil, eucalyptus oil, fennel oil, cinnamon oil, clove oil, geranium oil, sage oil, pimento oil, thyme oil, marjoram oil, basil oil, citrus oil or an isolated or synthetic component of these oils.

7. The composition of claim 1 containing an adduct of 20 to 60 mols of ethylene oxide with hardened or unhardened castor oil as a solubilizer.

8. Solid or liquid concentrates for making the preparations claimed in claim 1, wherein components A, B, C and D are present in such a concentration that the compositions are produced by dissolution in or dilution with water in a ratio by weight component to water of 1:1 to 1:500.

9. The composition of claim 1, wherein the biguanide is 1,1'-hexamethylene bis-(4-chlorophenyl)-biguanide in

TABLE 1

|  | 3.1 | 3.2 | 3.3 | 3.4 | 3.5 | 3.6 | 3.7 | 3.8 |
|---|---|---|---|---|---|---|---|---|
| Chlorhexidine digluconate | 0.015 | 0.015 | 0.015 | 0.015 | — | 0.015 | — | 0.015 |
| Isotridecyl glucoside (OG = 3.0) | 0.1 | 0.1 | 0.1 | 0.1 | 0.1 | — | — | 0.1 |
| Peppermint oil | 0.1 | 0.1 | — | — | 0.1 | 0.1 | 0.1 | 0.1 |
| HR 60 | 0.1 | — | 0.1 | — | 0.1 | 0.1 | 0.1 | 0.1 |
| Ethanol (99%, non-denatured) | 5.0 | 5.0 | 5.0 | 5.0 | 5.0 | 5.0 | 5.0 | 10.0 |
| Sorbitol (70%) | 3.0 | 3.0 | 3.0 | 3.0 | 3.0 | 3.0 | 3.0 | 3.0 |
| Saccharin sodium | 0.05 | 0.05 | 0.05 | 0.05 | 0.05 | 0.05 | 0.05 | 0.05 |
| Water | ad 100 | ad 100 | ad 100 | ad 100 | ad 100 | ad 100 | ad 100 | ad 100 |
| Remarks | clear | cloudy | bitter | bitter | clear | clear | clear | clear |
| Destruction times (minutes, subculture liquid) | | | | | | | | |
| Staphylococcus aureus | 5 | 1 | 15 | 1 | 15 | 15 | 15 | 1 |
| Steptococcus mutans | 2 | 5 | 15 | 1 | 15 | 15 | 15 | 5 |
| Residual germ content (contact time, subculture solid (agar nutrient medium)) | | | | | | | | |
| Staphylococcus aureus | −(1) | +(1) | +(2) | −(1) | ++(15) | +++(2) | +++(15) | −(1) |
| Steptococcus mutans | −(1) | −(1) | ++(1) | −(1) | +(15) | ++(2) | ++(15) | −(1) | the form of a water soluble physiologically compatible salt, the alkyl glycoside is one in which the alkyl contains from 8 to 14 carbon atoms and has at least one branch in the alkyl and an average degree of oligomerization of the glycoside component of from 1 to 41, and the water insoluble aromatic oil is selected from the group consisting of peppermint oil, spearmint oil, anise oil, star anise oil, caraway oil, eucalyptus oil, fennel oil, cinnamon oil, clove oil, geranium oil, sage oil, pimento oil, thyme oil, marjoram oil, basil oil, citrus oil or one or more isolated or synthetic components of these oils.

10. The composition of claim 9 containing an adduct of 20 to 60 mols of ethylene oxide with hardened or unhardened castor oil as a solubilizer.

* * * * *

UNITED STATES PATENT AND TRADEMARK OFFICE
CERTIFICATE OF CORRECTION

PATENT NO. : 4,923,685

DATED : 5-8-90

INVENTOR(S) : Wuelknitz et al.

It is certified that error appears in the above-identified patent and that said Letters Patent is hereby corrected as shown below:

At Claim 4, Column 6, line 25, "water-insoluble" should read --water-soluble--.

Signed and Sealed this

Twenty-third Day of June, 1992

*Attest:*

DOUGLAS B. COMER

*Attesting Officer*      *Acting Commissioner of Patents and Trademarks*